United States Patent [19]

Carr et al.

[11] Patent Number: 5,113,799

[45] Date of Patent: May 19, 1992

[54] METHOD AND APPARATUS FOR MASS PRODUCING INSECTS ENTOMOPATHOGENS AND ENTOMOPARASITES

[75] Inventors: Charles W. Carr, Edgewater; Douglas M. Kolodny-Hirsch, Fells Point, both of Md.

[73] Assignee: Crop Genetics International Corporation, Hanover, Md.

[21] Appl. No.: 527,954

[22] Filed: May 2, 1990

[51] Int. Cl.$^5$ .............................................. A01K 67/04
[52] U.S. Cl. .................................................. 119/6.5
[58] Field of Search .................... 119/6.5, 6.6, 15, 174

[56] References Cited

U.S. PATENT DOCUMENTS

| | | | |
|---|---|---|---|
| 2,137,769 | 11/1938 | Crawford. | |
| 2,539,633 | 1/1951 | Morrill. | |
| 3,468,289 | 9/1969 | Broida | 119/15 |
| 3,727,580 | 4/1973 | Yumiyama et al. | 119/6 |
| 3,750,625 | 8/1973 | Edwards | 119/1 |
| 3,874,335 | 4/1975 | Galasso | 119/15 X |
| 3,893,420 | 7/1975 | Andreev et al. | 119/6.6 |
| 4,252,080 | 2/1981 | Gioia et al. | 119/6.5 |
| 4,334,498 | 6/1982 | Bedding | 119/6.7 |
| 4,458,674 | 7/1984 | Lemburg et al. | 119/15 X |
| 4,572,427 | 2/1986 | Selfridge et al. | 236/3 |
| 4,594,964 | 6/1986 | Vargas et al. | 119/15 X |
| 4,765,274 | 8/1988 | Pizzol et al. | 119/6.6 |

FOREIGN PATENT DOCUMENTS

| | | | |
|---|---|---|---|
| 1020102 | 5/1983 | U.S.S.R. | 119/6.6 |
| 1028295 | 7/1983 | U.S.S.R. | 119/6.5 |
| 1230567 | 5/1986 | U.S.S.R. | 119/6.5 |

OTHER PUBLICATIONS

Bell, et al., Development of mass rearing technology, In C. C. Doane et al., (Eds.) The Gypsy Moth, U.S. Dept. Agriculture Tech Bull. 1584, pp. 599-633, 1981.
Shapiro, In vivo mass Production of insect viruses, In Microbialand viral pesticides. Kurstak, Ed., Marcel Dekker, NY, pp. 463-493, 1982.
Shapiro et al., In vitro mass production of gypsey moth NPV, In Doane et al., Eds, The Gypsy Moth, U.S. Dept. Agriculture Tech Bull. 1584, pp. 633-655, 1981.
E. S. Vanderzant, C. D. Richardson, S. W. Fort, Rearing of the Bollworm on Artifical Diet., Journal of Economic Entomology, 55, p. 140, 1962.

*Primary Examiner*—Gene Mancene
*Assistant Examiner*—Thomas Price
*Attorney, Agent, or Firm*—Finnegan, Henderson, Farabow, Garrett & Dunner

[57] ABSTRACT

This invention discloses a new apparatus for the rearing of insects and the production of insect related products, primarily insect viruses and parasites commonly used for the control of insect pests. The apparatus comprises an environmental control system, a sealed enclosure consisting of a hood and a base, and a system of vertically supported food leaves. The method of use is also disclosed. Use of this apparatus and method affords savings in labor and supplies.

48 Claims, 6 Drawing Sheets

METHOD AND APPARATUS FOR MASS PRODUCING INSECTS ENTOMOPATHOGENS AND ENTOMOPARASITES

BACKGROUND OF THE INVENTION

1. Field of the Invention

This invention relates to the field of apparatus for the rearing of insects, entomopathogens and entomophagous agents thereof, and products therefrom.

2. Description of Related Art

The term "entomopathogens" refers to viruses, bacteria, and fungi which infect insects. The term "entomophagous agents" refer to parasites which parasitize insects and predators which prey on insects.

Within the past 20 years, great advances have been made in both the production of insecticidal virus products (IVP) and the utilization of IVPs as safe and effective microbial control agents. Considerable research has led to the registration of four IVPs in the United States as microbial control agents. IVP production can be done in vitro (producing the virus in cell culture) or in vivo (producing the virus in the insect host). For the near term, in vivo production will remain the only practical alternative. The development of semi-synthetic diets facilitated successful mass rearing of hosts for in vivo production (Vanderzant et al). Later improvements in diet and refinement of insect host-virus-environmental factors have led to increased availability of IVPs (Shapiro). Regardless of the insect virus produced and the differences in methodology used by various workers, the basic production scheme involves insect diet/container preparation, insect growth, virus inoculation, virus incubation/larval maturation, and harvest of larvae. In the case of gypsy moth, *Lymantria dispar* L., production of this insect host and its *L. dispar* nuclear polyhedrosis virus (LdNPV) has been achieved using a system of carts, trays, and media-filled containers kept in rooms with controlled humidity and temperature. This system begins with the preparation of a high wheat-germ semisynthetic diet which is used as the rearing medium (Bell). Laboratory-reared eggs or their larvae are placed into 180-ml polyethylene cups (15 eggs or 10 larvae per cup) which are filled with 85 ml diet. For egg transfer, disinfected *L. dispar* eggmasses must be broken up and dehaired to free individual eggs. For neonate transfer, disinfected eggmasses are placed into 100-ml sterile petri dishes for hatching. After capping with paper lids, cups are placed onto 60×60 cm polyethylene trays (30 cups/tray), trays are placed horizontally onto 0.6×1.2×1.8 m mobile carts (18 trays/cart) and carts are wheeled to environmental chambers where insects are reared for 14 days at 26° C., 50% relative humidity (RH), and a photoperiod of 16:8 light:dark (L:D). Fourteen days later, carts are transferred from the environmental chambers, trays are removed from the carts, cups are removed from the trays, lids are removed from the cups, and the diet is surface treated with a viral suspension ($1.1 \times 10^3$ polyhedral inclusion bodies per mm$^2$. Subsequently, cups are recapped and placed back on carts in the aforementioned manner. Carts are transferred back to environmental chambers where insects and virus are incubated at 29° C., 50% RH and 16:8 L:D photoperiod (Shapiro et al). Fourteen days after infection, when larval mortality is about 75% (e.g. period when virus yield per larva and biological activity of harvested virus are maximal), carts are removed from the environmental chamber and placed in a freezer at −20° C. for 18 hours. Carts are then removed from the freezer, trays are removed from carts, cups are removed from trays, lids are removed from cups, and larvae are removed from the cups and are stored at −20° C. for subsequent extraction and processing of the virus. Freezing prior to harvest is a method for inhibiting bacterial growth within the insect, minimizing tissue histolysis and subsequent loss of virus by leakage into the diet, and synchronizing the production of virus. This rearing scheme allows insects to be reared on the same diet without transfer, with no adverse effects upon larval growth, virus yield, or virus activity. This method of virus propagation, however, has several drawbacks, such as, laborious repeated handling of cups; waste of insect media; inefficient use of space; and the expense of disposable rearing containers.

U.S. Pat. No. 3,727,580 discloses an apparatus for rearing silkworms on horizontal trays which are conveyed through the apparatus during the rearing process. U.S. Pat. No. 2,137,769 discloses a system in which provisions for maintaining desirable conditions of heat and humidity for an enclosure are located exterior to the enclosure. U.S. Pat. No. 2,539,633 discloses a device for breeding insects in which a vertical breeding tray is suspended by hooks and eyes from the top of the device. The breeding tray is constructed of wood or metal, has wire screening sides, and contains grain. U.S. Pat. No. 3,750,625 discloses a plastic insect breeding tray with multiple cup-like compartments and with egg receiving recesses connected to the cups by crawl passages. U.S. Pat. No. 4,572,427 discloses a controlled atmosphere enclosure with a recirculation path which includes a blower, a filter, a carbon dioxide sensor, and a humidifier. The system is controlled by a microprocessor.

The present invention overcomes the spatial/temporal drawbacks of conventional methods by providing a self-contained unit with a vertical array of media leaves and a computer controlled environment. Use of the invention involves performance of fewer functions on far fewer units than are required with the traditional rack/tray/cup system. The problems associated with contamination of cups with molds are avoided with this invention. This invention reduces the costs of producing insects, entomopathogens thereof, insect parasites, and other insect products.

SUMMARY OF THE INVENTION

We have discovered an improved method and apparatus for the mass production of insects and the propagation of their entomopathogenic and entomoparasitic agents. The process of the invention may be summarized as involving the following important steps:

1. The preparation of reinforced media leaves for feeding host insects;
2. The vertical array of media leaves for conserving space and improving insect access to media;
3. A environmental control system for altering environmental conditions in an enclosure;
4. The computerized monitoring and regulation of environmental conditions for optimizing insect and infectious agent growth and preserving freshness of media;
5. The removal of air-born microbial contaminants;
6. An enclosure for housing insects and media which facilitates insect establishment, pathogen/predator inoculation, and insect cadaver removal.

This invention may be used to produce a wide variety of insects; viruses, bacteria, and fungi which infect insects; parasites which parasitize insects; and predators which prey on insects. Some examples of the above are listed below. Some detailed examples of the use of this invention to produce the above are found in the section Description of the Preferred Embodiments.

Due to novel features of our invention, more host insects and their associated diseases, predators, and parasites can be mass reared per unit space while requiring less labor than traditional methods. With our method, less media is required than with the traditional method, resulting in further reduction of costs. Moreover, features of our computer controlled environment create a balanced microclimate which meets the maximum respiratory demands of the insects without promoting either excessive drying out or spoilage of the media. Because media leaves are hung vertically, and frass falls from the media surface, our method provides the host insect with improved access to the media, which results in improved growth. Our method is also suitable for application of automated media leaf preparation, virus inoculation, in-situ freezing, harvesting, and clean-up technologies.

The apparatus of the invention comprises: (a) an enclosure for media leaves and insects; (b) media leaves; (c) a life-support system comprising a heater, fan, HEPA filter, ductwork, sensors, and dampers; (d) computerized hardware and software for monitoring and regulating environmental conditions within the enclosure; (e) an array of rods for vertically suspending media leaves in a spaced parallel relationship; and (f) a centrally located rotating hub which supports the rods.

In the method of the invention, gypsy moth eggmasses are placed in an enclosure which contains an array of vertically supported media leaves. Upon hatching, neonates establish themselves on media leaves and are incubated at 29° C. for 14 days. A viral suspension is sprayed on the surface of the media leaves and 14 days later the virus has replicated within the larvae to produce 2,000 to 10,000 times more virus than originally used. Upon larval death, the contents of the unit are frozen, media leaves are removed, and cadavers are scraped from the media surface and are retained for further processing. The microclimate of the interior of the enclosure is carefully regulated for optimizing insect growth, maintaining biological activity of the virus, and preserving media freshness. Adequate air exchange is provided to remove toxic metabolic gases and to meet the maximal respiratory needs of the insect. The life-support system is equipped with HEPA filters to remove particles and microbial contaminants from incoming air.

It is an object of this invention to provide a device for mass propagation of a host insect and entomophagous or entomopathegenic agents.

Another object of this inventions is to provide an efficient, labor saving, and economical method for in vivo propagation of insects entomopathogens and entomophagous agents.

Another object of this invention is to provide a method for rearing insects on an industrial scale.

Another object of this invention is to provide insects with better access to media.

Another object of this invention is to provide a computer regulated microenvironment which promotes optimum insect and entomopathogen or entomophagous growth, ensures adequate removal of metabolic gasses, and provides an adequate air supply.

Another object of this invention is to provide a supply of filtered air free of contaminating infectious agents to the insects.

Other objects, features, and advantages of this invention will appear from the description given below referring to the attached drawings.

DESCRIPTION OF THE PREFERRED EMBODIMENTS

Figure 1:
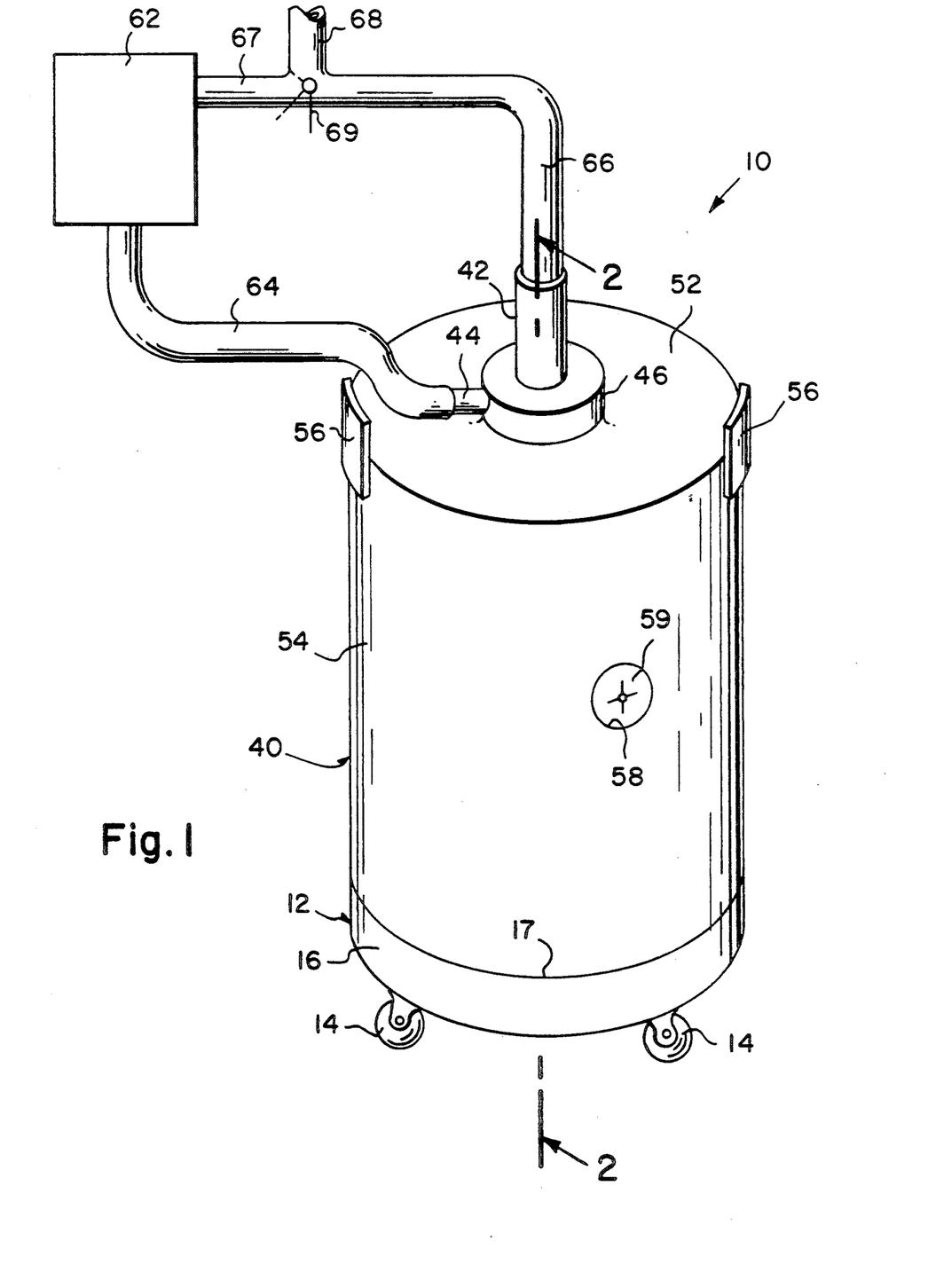
FIG. 1 is a perspective view of the outside of the apparatus.

FIG. 1 illustrates two of the the main components of the apparatus, the means for controlling the environment or environmental control system 62, and the enclosure 10 comprised of a cylindrical hood 40, and a base 12. These components are connected by ventilation tubes 64 and 66. The third main component of the apparatus, the food leaf support system and the food leaves is not shown in FIG. 1.

The means for controlling the environment or environmental control system 62 is illustrated schematically. It is a conventional system of the sort used to control industrial processes. The system contains a HEPA filter which filters microorganisms and other particles from the air stream before it leaves the environmental control system. The air is heated or cooled over a temperature range of 10° to 40° C. for insect rearing and may be heated to 100° C. for sterilizing of the apparatus. The humidity of the air is adjusted over a range of 0 to 100% relative humidity (RH). The volume of air provided by the environmental control system is 150 cubic feet a minute. The environmental control system is controlled by a 286 microprocessor computer.

The environmental control system may be equipped with sensors for gasses such as oxygen, carbon dioxide, and ammonia. Water potential in the media or pH or other chemical conditions in the media may also be monitored. The environmental control system functions to monitor conditions in the enclosure, adjust the environment in response to sensor readings or preset programming, record the conditions and responses, and display the recordings.

Figure 2:
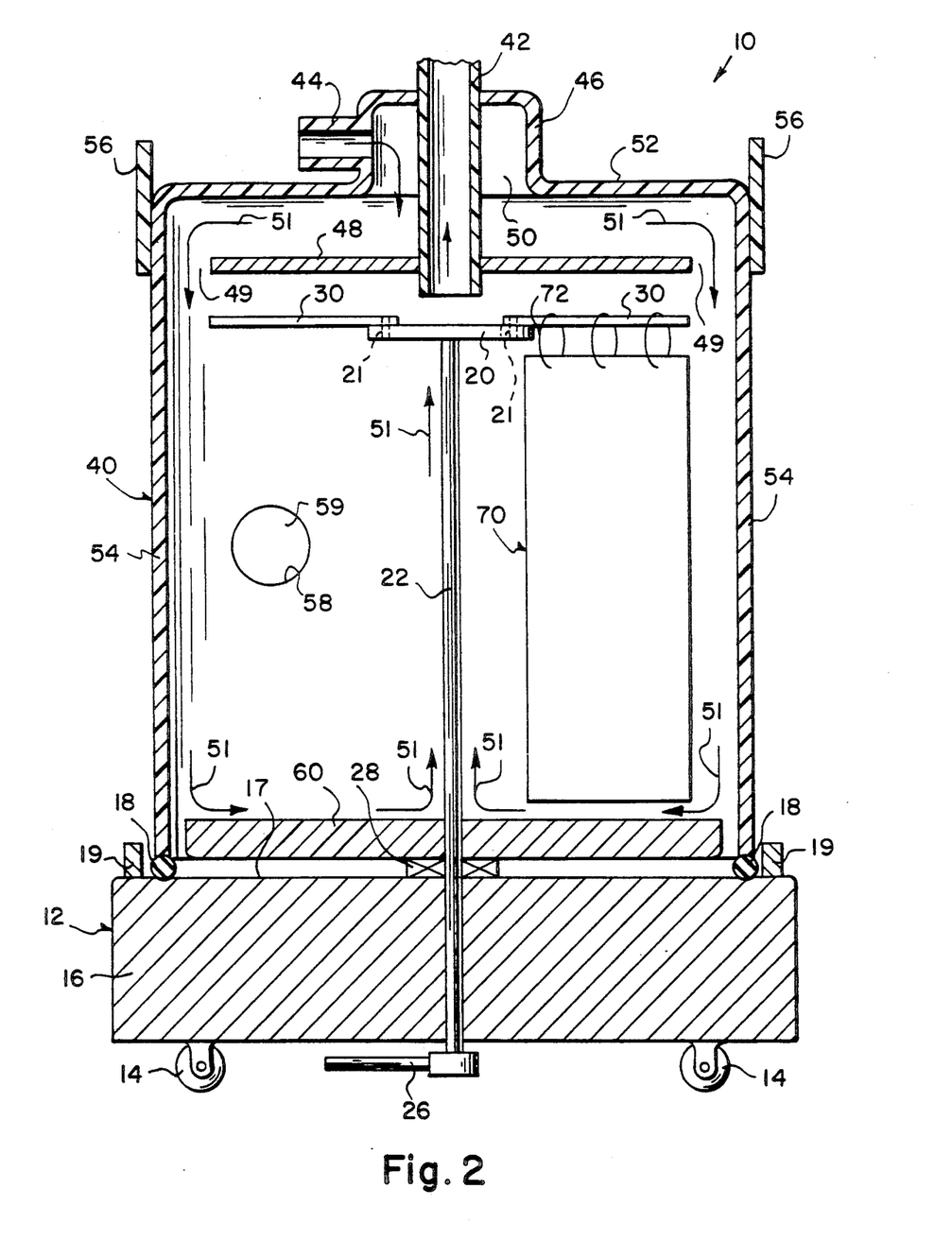
FIG. 2 is a cross sectional view of the first embodiment of the enclosure taken along line 2—2 of FIG. 1.

Air from the environmental control system is conveyed to the apparatus through the inlet tube 64 in FIGS. 1 and 2. The inlet duct 64 is connected to the entrance tube 44 which is connected to a cylindrical shaped plenum 46. The bottom of the plenum is open to the interior of the cylindrical hood 40 through a hole 50 in the top of the hood 52. The plenum serves to receive the air from the environmental control system 62 and to distribute it evenly into the hood 40. The plenum is pierced by the exhaust tube 42 which extends from the outside of the apparatus through the plenum and through a hole 50 in the top of the hood 52 to the interior of the hood. Air which has circulated through the hood 40 is collected by the exhaust tube 42 which is connected to the exhaust duct 66. Air which has entered the exhaust duct may be returned to the environmental control system through the recycle branch 67 or may be discharged to the atmosphere through the discard branch 68. A damper 69 is used to determine the proportion of air which is recycled and discarded.

The flow of air within the hood is shown in more detail FIG. 2. A disc shaped diffuser plate 48 is attached to the end of the exhaust tube 42 inside the hood 40. Air enters the hood through the plenum 46 and is distributed evenly over the upper surface of the diffuser plate 48. The air flows to the edge of the diffuses plate and flows down through the gap 49 between the diffuser plate 48 and the wall of the hood 54. The air flow follows the wall of the hood 54 to the bottom of the hood where it flows toward the center of the hood and upwardly toward the exhaust tube 42. Thus the cylindrical shaped apparatus is ventilated by a flow of air which enters at the top, flows down the sides of the hood, flows up the center of the apparatus, and exits from the top, as shown by arrows 51.

The hood 40 is a cylindrical structure having a top 52, a wall 54, and an open bottom. Two brackets 56 attached to the wall of the hood allow the hood to be raised using a block and tackle (not shown). Portholes 58 which may be sealed by porthole covers 59 allow access to the interior of the hood. The hood is constructed of Plexiglass, a trademark owned by Rohm and Haas for its brand of polymethylmethacrylate but may be made of any suitable material having the properties of strength, durability, resistance to corrosion and non toxicity.

The base 12 consists of a cylindrical steel platform 16 with four wheels 14 attached to the bottom and a stainless steel top 17. The wheels provide mobility for the enclosure, which may be placed in a freezer, for example. A rubber gasket 18 rests on the top 17 of the base and seals the connection between the base and the open bottom of the hood which rests on the base 12, thus forming a sealed hood. Four studs 19 aid in the alignment of the hood. A circular shaped pan 60 with raised edges fits on the base inside the hood. The pan receives frass and insects which have fallen from the food leaves when the apparatus is in use.

Figure 4:
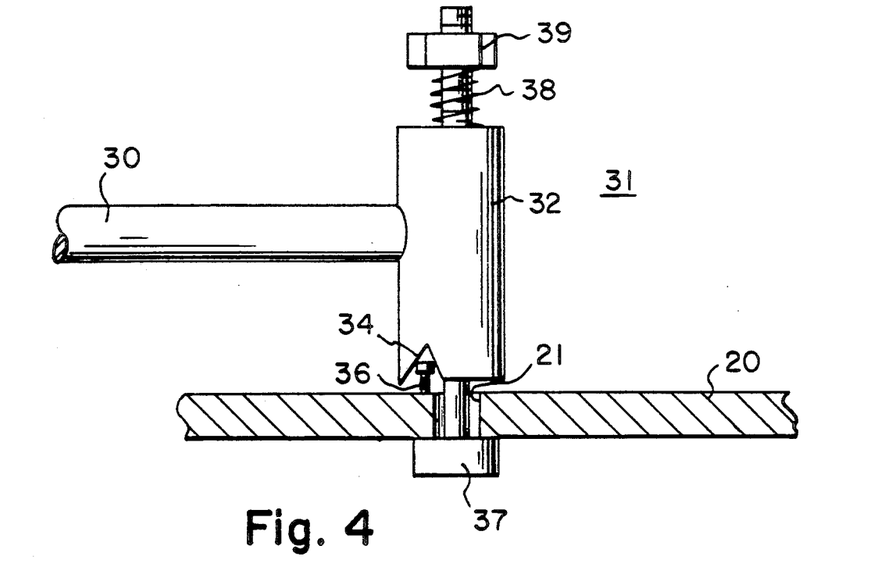
FIG. 4 is a plan view showing attachment of an outrigger to the hub.

The food leaf supporting system is supported by a vertical bar or shaft 22 having a top and a bottom end which is journaled in the center of the base and generally extends vertically through the center of the apparatus to near the exhaust tube and diffuser plate. At the top end of the shaft a disc-shaped hub 20 is mounted. Seventy-two holes 21 are evenly distributed about the margin of the hub. Outriggers are resilient rods which support the food leafs. One outrigger is mounted in each hole in the hub. Each outrigger 30 supports one food leaf. The details of the outrigger and outrigger attachment by means of self-centering mounts 31 are shown in FIG. 4. Each outrigger 30 is attached at one end to the side of a connector 32. A connector is a short tube with a v-shaped notch 34 at one end. A screw 23 protrudes from the hub 20 adjacent to the hole 21 and between the hole and the margin of the hub. The connector is mounted on the hub 20 by a bolt 37 which protrudes through the hub 20, through the connector 32, and is secured by a nut 39. The notch 34 is engaged by the screw 23. The connector 32 is biased downwardly toward the hub by a spring 38 interspersed between the end of the connector 32 and the nut 39. Thus the outrigger is biased by the spring so that the screw 36 rests in the notch 34. This allows the outrigger to be swung through an arc of 180° while tending to return to a rest position along a radius of the hub. This allows to outriggers and connected food leaves to be swung for examination and manipulation during the use of the apparatus.

The shaft 22 may be rotated in order to move the food leaves. A rachet 28 is connected to the shaft 22 at the bottom end where it extends through the bottom of the base. A handle 26 is used to facilitate rotation of the shaft 22.

Figure 3:
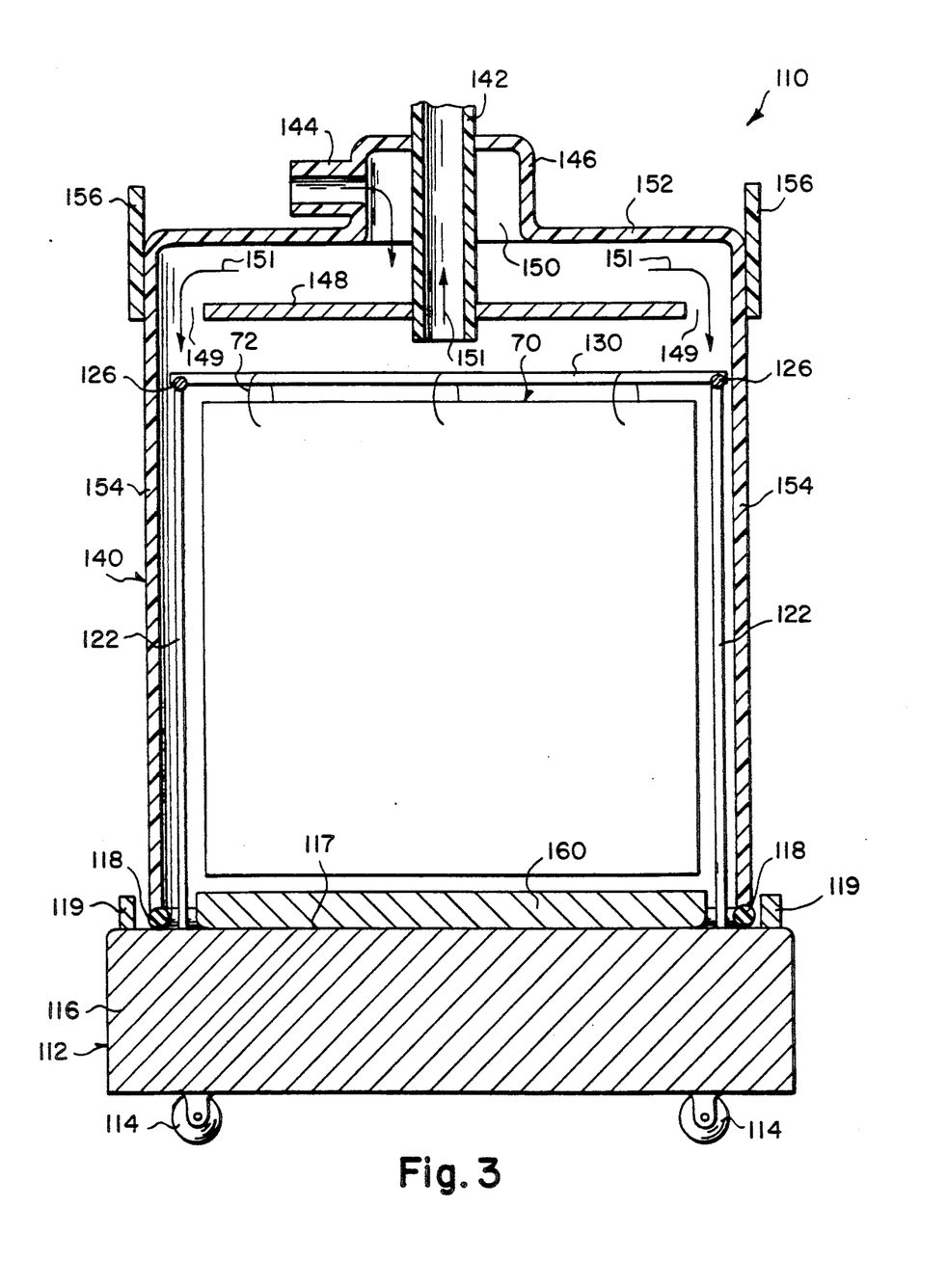
FIG. 3 is a cross sectional view of the second embodiment of the enclosure.

In a second embodiment, the enclosure is rectangular in shape and is shown in cross section in FIG. 3. Outriggers 130 are attached by ties 72 at the top of the food leaves 70. The outriggers are supported on each end by the side pieces 126 of a leaf supporting system consisting of side pieces 126 attached to end pieces 124, thus forming a rectangular frame structure, which is supported by four legs 122.

Figure 5:
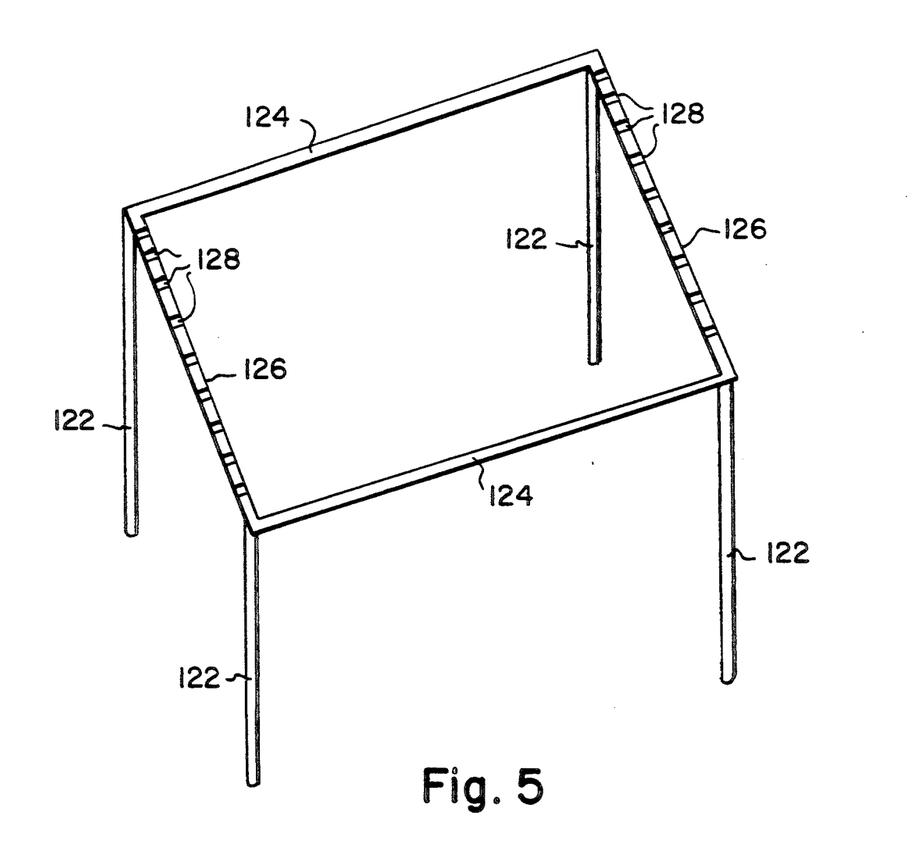
FIG. 5 is a plan view of the second embodiment of the leaf support system.

The leaf support system of the second embodiment is shown in FIG. 5. A rectangular framework consisting of two end pieces 124 and two side pieces 126 is supported by four legs 122. Seventy two notches 128 are arrayed along each side piece. The notches serve to stabilize the outriggers which extend across the the leaf support system and are supported by the side pieces. A rectangular shaped pan 160 with raised edges fits on the base inside the hood.

Air from the environmental control system is conveyed to and from the enclosure of the second embodiment as in the first embodiment. In the second embodiment, the inlet duct 64 is connected to the inlet tube 144 which is connected to a cylindrical shaped plenum 146. The bottom of the plenum is open to the interior of the hood 140 through a hole 150 in the top of the hood 152. The plenum serves to receive the air from the environmental control system 62 and to distribute it evenly into the hood 140. The plenum is pierced by the exhaust tube 142 which extends from the outside of the apparatus through the plenum and through a hole 150 in the top of the hood 152 to the interior of the hood. Air which has circulated through the hood 140 is collected by the exhaust tube 142 which is connected to the exhaust duct 66.

FIGS. 6A to 10B show five embodiments of the food leaves.

Figure 6A:
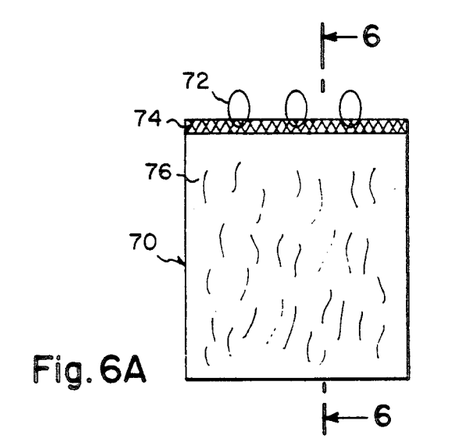
FIG. 6A is a plan view of the first food leaf embodiment.
Figure 6B:
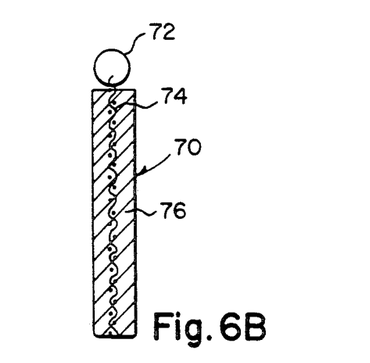
FIG. 6B is a cross sectional view of the embodiment taken along line 6—6 of FIG. 6A.

In the first embodiment, FIGS. 6A and 6B, the gelled food leaf 70, a support mesh 74 or strip is coated on both sides with thermoplastic food 74 which gels when cooled to room temperature. Three ties 72, hooks, or other suitable attachment means protrude through holes in the support mesh 74 and serve to reversibly attach the food leaf to an outrigger 30, FIG. 2 or rod 130 FIG. 3. The leaf is supported in a substantially vertical position with the long axis perpendicular to the apparatus base.

Figure 7A:
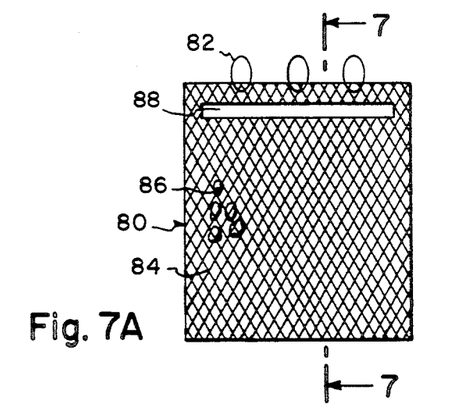
FIG. 7A is a plan view of the second food leaf embodiment.
Figure 7B:
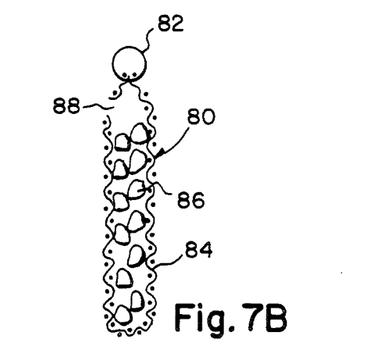
FIG. 7B is a cross sectional view of the embodiment taken along line 7—7 of FIG. 7A.

In the second embodiment, FIGS. 7A and 7B, the bagged food leaf 80, a mesh bag 84 constructed of plastic mesh and rectangular is shape is used to contain and support food particles 86 which are in the size range of 0.5 to 3.0 cm in diameter. An opening 88 at the top of the bag provides access to the interior of the bag for loading the bag leaf with food particles. Ties 82 protrude through the mesh and attach the leaf as in the first embodiment.

Figure 8A:
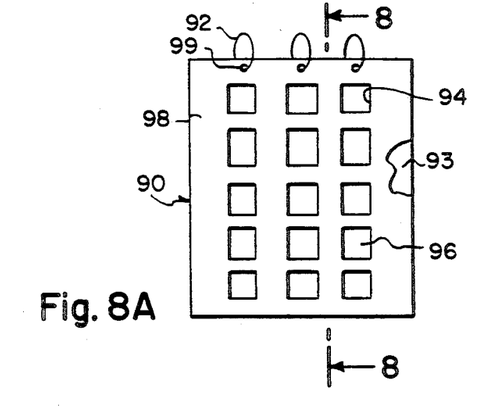
FIG. 8A is a plan view of the third food leaf embodiment.
Figure 8B:
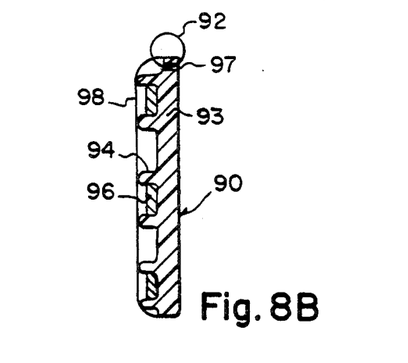
FIG. 8B is a cross sectional view of the embodiment taken along line 8—8 of FIG. 8A.

In the third food leaf embodiment, FIGS. 8A and 8B, the individual cell food leaf 90, a plastic support sheet 93 supports 32 cylindrical-shaped cells 94 each of which is formed as part of the support sheet or is attached to the support sheet. A supply of gelled food 96 is provided in each cell 94. A cover of plastic shrink film 98 is used to close the individual cells after each have been inoculated with a single insect egg or immature stage. Ties 92 protrude through holes 97 in the support sheet 93 and attach the leaf as in the first embodiment.

Figure 9A:
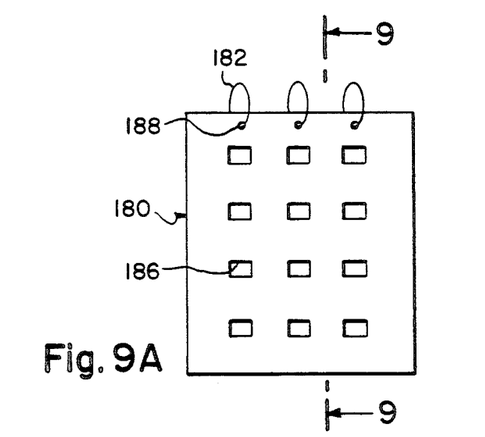
FIG. 9A is a plan view of the fourth food leaf embodiment.
Figure 9B:
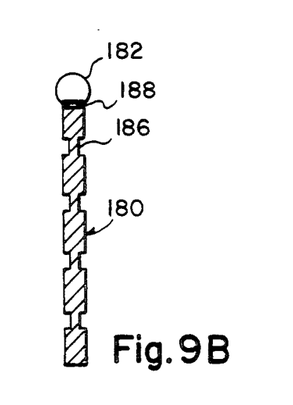
FIG. 9B is a cross sectional view of the embodiment taken along line 9—9 of FIG. 9A.

In the fourth food leaf embodiment, FIGS. 9A and 9B, the waffle food leaf 180, a waffle 180 is formed of food which has been cooked or baked to provide a rectangularly-shaped dry biscuit of solidified food of strength adequate to support its weight when suspended from a leaf support system. Rectangular depressions or indentations 186 are formed in the cooking or baking process and serve to increase the surface area of the waffle thereby facilitating its consumption. The waffle embodiment also may be formed without indentations. Ties 182 protrude through holes 188 through the waffle 180 and attach the leaf as in the first embodiment.

Figure 10A:
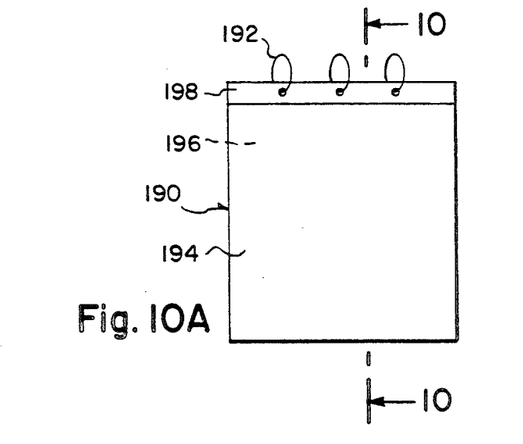
FIG. 10A is a plan view of the fifth food leaf embodiment.
Figure 10B:
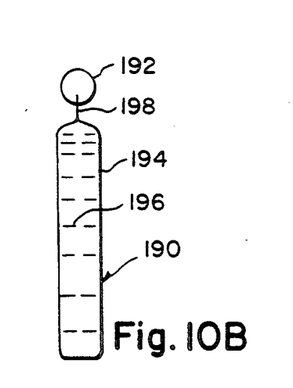
FIG. 10B is a cross sectional view of the embodiment taken along line 10—10 of FIG. 10A.

In the fifth embodiment, FIGS. 10A and 10B, the liquid leaf, a thin, liquid impervious, penetrably membrane 194 is used in the form of a bag to contain liquid food 196. The opening at the top of the bag is sealed at the top 198. Ties 192 protrude through holes in the seal and attach the leaf as in the first embodiment.

The ties or hooks which attach the leaves may be constructed of any suitable strong, resilient, corrosion resistant non toxic materials such as plastic or stainless steel. In the preferred embodiment, plastic cable connector ties are used.

The mesh or sheets of the first and third food leaf embodiments may be constructed of any suitable inert non toxic material such as polystyrene, or polyethylene.

The mesh bag of the second embodiment may be constructed of any suitable strong, flexible non toxic material not susceptible to corrosion such as polyethylene or stainless steel. Wire screening or hardware cloth is not suitable due to corrosion in the high humidity environment of the enclosure.

The impervious membrane of the fifth embodiment may be any suitable material such as latex which will retain the liquid food yet be penetrable by the piercing-sucking mouthparts of insects which feed on a liquid diet.

Food leaves were prepared in the following manner.

Embodiment 1 used the medium in Table 1 for the preparation of food leaves for use in rearing gypsy moths.

TABLE 1

| Ingredient | Gram/liter |
|---|---|
| Wheat germ | 120 |
| Casein | 25 |
| Agar | 15 |
| Wesson salt mixture | 8 |
| Sorbic acid | 2 |
| Methyl paraben | 2 |
| Calcium propionate | 2 |
| Vitamin premix | 10 |
| Water | 800 |

The Wesson salt mixture contained the following in percent by weight; calcium carbonate, 21.000; copper sulfate - $5H_2O$, 0.039; ferric phosphate, 1.470; manganous sulfate, 0.020; magnesium sulfate - $7H_2O$, 9.000; potassium aluminum sulfate, 0.009; potassium chloride, 12.000; potassium phosphate monobasic, 31.000; potassium iodide, 0.005; sodium chloride, 10.500; sodium fluoride, 0.057; and tricalcium phosphate, 14.900. The Wesson salt mixture was obtained from ICN Chemicals, Division of ICN Biochemicals, Inc., Cleveland, Ohio, 44128.

The vitamin premix was USDA Vitamin Premix, Code No. 272686200, obtained from Roche Chemical Division, Hoffman-LaRoche, Inc., Nutley, N.J., 07110.

A medium form was made of masonite with a length of 152 cm, width of 30.5 cm, and height of 2.5 cm. The form was lined with freezer paper. A piece of plastic hardware cloth mesh 30.5 by 157 cm was placed in the form with excess mesh extending at one end. The medium of Table 1 was mixed, sterilized by heating in an autoclave at 121° C. for 15 minutes, allowed to cool to approximately 50° C. and, while still molten, poured into the form. After cooling for 1 hour, the food leaf comprised of medium solidified on a mesh framework was removed from the form. The leaf was attached to an outrigger with 3 nylon ties through the mesh at one end of the leaf.

Embodiment 2 uses particulate food such as grain, vegetables such as cabbage or lettuce, leaves such as mulberry leaves prepared food such as rabbit rations or dog food, or dried meat.

Embodiment 3 uses the formula of embodiment 1.

Embodiment 4 uses about 225 ml of the dry ingredients of Table 1 without agar added to 300 ml water. This mixture was stirred forming a batter. The batter was baked on a waffle iron for 5 minutes or until dry and crispy. In a variation, about 200 ml of the dry ingredients of Table 1 without agar were mixed with 30 ml cornstarch and 200 ml water. The mixture was heated to boiling and cooked for 2 minutes. The mixture was cooled to room temperature and 3 egg whites were added and mixed. The mixture was spread on an aluminum foil-lined cookie sheet and baked in an oven at about 232° C. for 5 minutes. The temperature of the oven was reduced to about 204° C. and baking was continued for another 5 minutes. Holes were drilled into the resulting waffle at one end and ties were inserted.

Embodiment 5 uses suitable liquid diet for the insect to be reared, such as blood for the rearing of mosquitoes.

Although specific media formulations have been disclosed, it will be noted that media compositions may be modified to accommodate the specific requirements of the insects being reared.

EXAMPLE 1

The virus LdPNV was produced in a colonized strain of the insect *Lymantria dispar*. The apparatus was charged with food leaves prepared as in embodiment 1 above. Seventy-two food leaves were attached to outriggers using nylon ties. The environmental control system was used to ventilate the apparatus and to maintain the environment at about 30° C. V and 92% RH. Twenty-five paper towels each of which had 20 *L. dispar* eggmasses attached were used to inoculate the apparatus. One paper towel was attached to every third or fourth outrigger. After 14 days of incubation the eggs had hatched, the insects had colonized substantially the entire surface of the food leaves, and the insects had reached the fourth instar of development. The larvae were infected with LdNPV by spraying each side of each food leaf with virus suspended in water at $1.1 \times 10^3$ polyhedral inclusion bodies/mm² leaf surface. The inoculated larvae were incubated an additional 14 days to allow viral multiplication. The hood and base were detached from the environmental control unit and were placed in a freezer at $-20°$ F. for 24 hours. The hood and base were removed from the freezer and the hood was lifted using a block and tackle. The food leaves were detached from the outriggers and the larvae cadavers were harvested by suction with a wet/dry vacuum cleaner. Cadavers were also collected from the pan and from the interior surfaces of the enclosure. Cadavers were processed further to concentrate and to purify the LdNPV.

EXAMPLE 2

Silk may be produced using the apparatus as follows. The apparatus is charged with mulberry food leaves as in embodiment 2 above. The environmental control system is used to ventilate the apparatus and to maintain the environment at 24 ° C. and 65% RH. Sufficient number of eggmasses are placed at the bottom of the hood to yield 50,000 young larvae. Clean fresh leaves are added to the unit daily. When most larvae moves to the new leaves, the old foliage is removed. As the larvae grow they are fed progressively older, tougher foliage. The silkworms spin cocoon in 23 days. Long pieces of paper towel are loosely crumbled and placed in the bags of embodiment 2 in order to provide spinning sites. Cocoons are spun and pupation occurs in about 3 days. When the cocoons are quite firm, the hood is lifted as described in Example 1. The leaves are detached and the cocoons harvested.

Other examples of insects and insect products which may be produced using the present invention are described below.

A wide variety of insect pathogens or parasites are produced by infection of insect larvae or eggs. Nematodes are produced in larvae of the wax moth *Galleria mellonella*. *Steinernema feltiae* nematodes are produced on various insect pests such as the larvae of *G. mellonella* or on artifical diet. *Heterorhabditis heliothidis* is produced on the blackvine weevil.

Parasitic mites are produced on grain moths. Eggs of flour moth *Ephestia kuhniella* are parasitized by Trichogramma spp. oophage parasites. Aphids are parasitized by the parasitic wasp *Braconid lysiphelebus*. The walnut aphid *Chromaphis juglandicolo* is used to produce the braconid wasp *Trioxys pallidus*. Some insect parasites may be reared directly on artificial diets, for example the ichneumonid ectoparasite *Exeristes roborator*.

Several species of protozans are mass-reared on insect hosts. *Vairimorpha necatrix* are reared on *Heliothis virescens*. *Nosema locusta* are produced on grasshoppers.

Viruses which may be produced by infection of larvae or eggs include the following: production of LpNVP in gypsy moth, production of *Orygia pseudotsugata* nuclear polyhedrosis virus (OpNPV) in Douglas-fir tussock moth, and production of OpNPV in whitemarked tussock moth, *Orygia leucostigma*.

Insects per se are often mass produced. The production and release of insects made sterile by gamma irradiation has been developed to control numerous important insect pest species. These include screw-worm flies, *Cochliomyia houinivorax*, various fruit flies, cotton boll weevil, and codling moth.

Coccinellid predators may be produced in aphids.

Recent findings suggest a future need for the production of insects for the production of non-insect proteins and other metabolites in insects which have been genetically altered by gene transfer through genetic engineering.

Although the invention has been described in some detail by way of illustration and example for purposes of clarity of understanding, it will be obvious that certain changes and modifications may be practices within the scope of the appended claims.

We claim:

1. An apparatus for producing entomopathogens or entomoparasites comprising,
   a base,
   a hood mounted on the base,
   means for controlling the environment within the hood,
   means for positioning leaves inside the hood, and
   leaves positioned inside the hood.

2. The apparatus of claim 1 wherein the leaves comprise a composite of gelled food and a supportive material.

3. The apparatus of claim 1 wherein the leaves comprise food particles contained in a mesh bag.

4. The apparatus of claim 1 wherein the leaves comprise a support sheet having on its surface individual cells containing gelled food.

5. The apparatus of claim 1 wherein the leaves comprise solidified food.

6. The apparatus of claim 1 wherein the leaves comprise liquid food contained in liquid-impervious, penetrable bags.

7. The apparatus of claim 1 wherein the hood is removable.

8. The apparatus of claim 1 further comprising means on the base for moving the apparatus.

9. The apparatus of claim 1 wherein the means for controlling the environment comprise means for providing conditions within the hood suitable for rearing insects.

10. The apparatus of claim 1 wherein the means for controlling the environment comprise means for providing the hood with filtered air of controlled temperature and humidity suitable for rearing insects.

11. The apparatus of claim 1 wherein the means for controlling the environment within the hood further comprise an inlet, a plenum, a diffuser plate, and an exhaust.

12. The apparatus of claim 1 wherein the hood is cylindrical in shape.

13. The apparatus of claim 12 wherein the means for supporting the leaves comprise a hub supported within the hood, and a multiplicity of outriggers for supporting the leaves attached to the margin of the hub.

14. The apparatus of claim 12 wherein the outriggers are attached to the margin of the hub by self-centering mounts.

15. The apparatus of claim 12 further comprising means for rotating the hub.

16. An apparatus of claim 1 wherein the hood and the base are rectangular in shape.

17. The apparatus of claim 16 wherein the means for vertically suspending leaves comprises outriggers, a outrigger support frame which supports the outriggers, and legs which support the outrigger support frame.

18. The apparatus of claim 1 further comprising a pan which fits on the base inside the hood for receiving frass and fallen insects.

19. The apparatus of claim 1, further comprising means for portably transporting said apparatus.

20. The apparatus of claim 19, wherein said means comprises wheels.

21. The apparatus of claim 1, wherein said leaves are vertically positioned inside the hood.

22. An apparatus for rearing insects comprising,
an environmental control system for delivering air comprised of a HEPA filter for filtering air, means for controlling the relative humidity of air between 0 to 100% RH, means for controlling the temperature of air between 10° and 100° C., means for recycling air within the environmental control system, sensors to measure the relative humidity and temperature of the air, and a microprocessor for sensing, adjusting, recording, and displaying the conditions of the air,
a cylindrical hood made of polymethylmethacrylate having a closed top, an open bottom, a cylindrical wall having portholes and porthole covers, the closed top having a cylindrical-shaped plenum on the outside of the top, the bottom of the plenum open to the interior of the hood through a hole in the top of the hood, an inlet tube connected to the plenum, an exhaust tube piercing the top of the plenum and extending through the hole in the top of the hood into the interior of the hood, a diffuser plate attached to the exhaust tube on the inside of the hood, and two brackets attached to the wall for lifting the hood,
an inlet connecting the environmental control system and the inlet tube connected to the plenum,
an exhaust duct connected to the exhaust tube on the outside of the hood which returns air to the environmental control system, a discard branch connected to the exhaust duct, a damper connected to the exhaust duct, recycle branch and discard branch,
a base comprised of a cylindrical steel platform having wheels and a stainless steel top, a rubber gasket on the top for sealing the connection between the base and the bottom of the hood, and studs which aid in alignment of the hood and base, and a pan with raised edges which fits on the base inside the hood,
a leaf supporting system comprising, a shaft having a top and bottom end journaled through the center of the base and extending vertically through the center of the apparatus, a ratchet attached to the bottom end of the shaft at the bottom of the base, a handle attached to the ratchet for rotating the shaft, a disc-shaped hub having a multiplicity of holes arrayed about the margin of the hub mounted at the top end of the shaft, an outrigger attached by a self-centering mount in each hole in the hub, the self-centering mount comprising a connector with a v-shaped notch, a screw protruding from the hub between the hole and margin of the hub, a bolt and nut attaching the connector to the hub, and a spring which biases the v-shaped notch against the screw, and
a multiplicity of leaves, each attached to one outrigger by nylon ties, each leaf comprised of gelled food coated on a mesh support, food particles contained in a mesh bag, gelled food in individual cells on a sheet, solidified food in a waffle, or liquid food in a bag.

23. The process of producing entomopathogens or entomoparasites comprising the steps;
charging an apparatus for rearing insects with leaves,
inoculating the apparatus with eggs or immature phases of the insects,
ventilating the apparatus with air at temperature and humidity suited for the rearing of the insects,
incubating for a duration of time adequate to rearing the insects, and
harvesting the insects or products of their rearing.

24. The process of claim 23 wherein the insects are silkworms and the product of their rearing is silk.

25. The process of claim 23 further comprising the step, introducing into the hood entomopathogens viruses, bacteria, fungi, parasites, or predators.

26. The process of claim 25 wherein the insects are Lepidoptera species and the virus introduced into the hood is a baculovirus.

27. The process of claim 25 wherein the insects are gypsy moths, *Lymantria dispar*, and the virus introduced into the hood is *Lymantria dispar* nuclearpolyhedrosis virus.

28. The process of claim 25 wherein the insects are Douglas-fir tussock moth, *Orygia pseudotsugata*, and the virus introduced into the hood is *Orygia pseudotsugata* nuclearpolyhedrosis virus.

29. The process of claim 25 wherein the insects are white-marked tussock moths, *Orygia leucostigma*, and the virus introduced into the hood is *Orygia leucostigma* nuclearpolyhedrosis virus.

30. A method for producing entomopathogens comprising the steps of:
(a) introducing insects or insect eggs or larvae within an enclosure;
(b) inoculating said insects or insect eggs or larvae with an entomopathogen;
(c) monitoring an environment within said enclosure with a computer;
(d) incubating said insects or insect eggs or larvae and said entomopathogen for a time sufficient for said entomopathogen to multiply;
(e) regulating said environment during said incubating step by feedback from said monitoring step; and
(f) harvesting entomopathogen-containing insects or insect eggs or larvae.

31. The method of claim 30, wherein said insects or insect eggs or larvae are from the Lepidoptera species.

32. The method of claim 31, wherein said insects or insect eggs or larvae are of *Lymantria dispar*.

33. The method of claim 30, wherein said entomopathogen is a virus.

34. The method of claim 33, wherein said virus is a baculovirus.

35. The method of claim 34, wherein said baculovirus is a nuclearpolyhedrosis virus.

36. The method of claim 30, wherein said monitoring step comprises monitoring temperature and humidity.

37. The method of claim 36, wherein said monitoring step comprises monitoring gases within said enclosure.

38. The method of claim 30, wherein said incubating step further comprises providing leaves for said insects or insect eggs or larvae.

39. A method for producing entomoparasites comprising the steps of:
(a) introducing insects or insect eggs or larvae within an enclosure;
(b) inoculating said insects or insect eggs or larvae with an entomoparasite;
(c) monitoring an environment within said enclosure with a computer;
(d) incubating said insects or insect eggs or larvae and said entomoparasite for a time sufficient for said entomoparasite to multiply;
(e) regulating said environment during said incubating step by feedback from said monitoring step; and
(f) harvesting entomoparasite-containing insects or insect eggs or larvae.

40. The method of claim 39, wherein said monitoring step comprises monitoring temperature and humidity.

41. The method of claim 40, wherein said monitoring step comprises monitoring gases within said enclosure.

42. The method of claim 39, wherein said incubating step further comprises providing leaves for said insects or insect eggs or larvae.

43. The method of claim 39, wherein said entomoparasite is a nematode.

44. The method of claim 39, wherein said entomoparasite is an aphid.

45. The method of claim 39, wherein said entomoparasite is a protozoan.

46. The method of claims 30 or 39, wherein said regulating step comprises providing filtered air free of contaminating agents.

47. The method of claim 46, wherein said filtered air is filtered by a HEPA filter.

48. The method of claim 46, wherein said filtered air flows in a laminar fashion in said enclosure.

* * * * *